(12) United States Patent
Meiring et al.

(10) Patent No.: US 12,042,551 B2
(45) Date of Patent: Jul. 23, 2024

(54) ALKANE DIOLS IN SALT-CONTAINING COSMETIC PREPARATIONS

(71) Applicant: BEIERSDORF AG, Hamburg (DE)

(72) Inventors: Uta Meiring, Hamburg (DE); Jan Nilsson, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 347 days.

(21) Appl. No.: 16/619,513

(22) PCT Filed: Jun. 4, 2018

(86) PCT No.: PCT/EP2018/064550
§ 371 (c)(1),
(2) Date: Dec. 5, 2019

(87) PCT Pub. No.: WO2018/224413
PCT Pub. Date: Dec. 13, 2018

(65) Prior Publication Data
US 2020/0093718 A1 Mar. 26, 2020

(30) Foreign Application Priority Data
Jun. 8, 2017 (DE) .......................... 102017209649.7

(51) Int. Cl.
| | | |
|---|---|---|
| *A61K 8/34* | (2006.01) | |
| *A61K 8/02* | (2006.01) | |
| *A61K 8/06* | (2006.01) | |
| *A61K 8/20* | (2006.01) | |
| *A61K 8/81* | (2006.01) | |
| *A61Q 19/10* | (2006.01) | |

(52) U.S. Cl.
CPC ............ *A61K 8/345* (2013.01); *A61K 8/0208* (2013.01); *A61K 8/062* (2013.01); *A61K 8/20* (2013.01); *A61K 8/347* (2013.01); *A61K 8/8152* (2013.01); *A61K 8/8182* (2013.01); *A61Q 19/10* (2013.01); *A61K 2800/30* (2013.01); *A61K 2800/59* (2013.01)

(58) Field of Classification Search
CPC .... A61K 8/345; A61K 8/375; A61K 2800/30; A61K 8/347; A61K 2800/59; A61K 8/34; A61K 8/0208
See application file for complete search history.

(56) References Cited

U.S. PATENT DOCUMENTS

| | | | | |
|---|---|---|---|---|
| 4,704,226 | A | * 11/1987 | Naylor ..................... | A61K 8/44 424/70.24 |
| 5,756,112 | A | 5/1998 | Mackey | |
| 5,863,663 | A | 1/1999 | Mackey | |
| 6,248,340 | B1 | 6/2001 | Maor | |
| 8,410,037 | B2 | * 4/2013 | Molenda ................... | A61Q 5/02 510/122 |
| 2004/0081672 | A1 | * 4/2004 | Gupta ................... | A61K 31/455 424/401 |
| 2005/0002994 | A1 | 1/2005 | Goppel | |
| 2005/0186164 | A1 | * 8/2005 | Akyuz ..................... | A61K 8/731 424/70.2 |
| 2005/0238610 | A1 | * 10/2005 | Nielsen ................... | A61Q 17/04 424/70.31 |
| 2006/0079431 | A1 | * 4/2006 | Lal ........................ | C11D 1/002 510/421 |
| 2006/0210612 | A1 | * 9/2006 | Simon ..................... | A61Q 1/14 424/443 |
| 2008/0131470 | A1 | 6/2008 | Witham | |
| 2010/0197544 | A1 | * 8/2010 | De La Cruz ......... | A61Q 19/005 510/157 |
| 2017/0173162 | A1 | * 6/2017 | Jiao ........................ | A61K 8/922 |
| 2017/0281525 | A1 | 10/2017 | Pham | |
| 2018/0140527 | A1 | * 5/2018 | Tian ........................ | A61P 43/00 |

FOREIGN PATENT DOCUMENTS

| | | |
|---|---|---|
| AT | 507845 A1 | 8/2010 |
| CN | 106176442 A | 12/2016 |
| DE | 69506912 T2 | 5/1999 |
| DE | 69601705 T2 | 8/1999 |
| DE | 10154627 A1 | 5/2003 |
| DE | 10234256 A1 | 2/2004 |
| DE | 102010006612 A1 | 8/2011 |
| EP | 0937453 A2 | 8/1999 |
| EP | 1334715 A2 | 8/2003 |
| WO | 9902128 A1 | 1/1999 |
| WO | 2008057442 A2 | 5/2008 |
| WO | 2017173030 A1 | 10/2017 |

* cited by examiner

*Primary Examiner* — Jianfeng Song
(74) *Attorney, Agent, or Firm* — Abel Schillinger, LLP

(57) ABSTRACT

Cosmetic preparation containing a) one or more alkane diols selected from the group of the compounds propylene glycol, butylene glycol, 2-methylpropane-1,3-diol, ethylhexylglycerol, 1,2-pentanediol, 1,2-hexanediol, 1,2-octanediol and/or 1,2-decanediol, and b) sodium chloride in a concentration of 0.25 to 5% by weight, based on the total weight of the preparation.

20 Claims, No Drawings

ALKANE DIOLS IN SALT-CONTAINING COSMETIC PREPARATIONS

BACKGROUND OF THE INVENTION

1. Field of the Invention

The present invention relates to a cosmetic preparation comprising one or more alkane diols and sodium chloride, as well as a cleansing wipe, which is impregnated with this preparation.

2. Discussion of Background Information

The desire to look beautiful and attractive is naturally rooted in humans. Although ideals of beauty have changed over time, the pursuit of a flawless appearance has always been aimed for by humans. An essential part of a beautiful and attractive appearance is the condition and complexion of the skin.

In order for the skin to be able to perform the full range of its biological functions, it requires regular cleansing and care. Cleansing of the skin serves to remove dirt, sweat and residual dead skin particles, which form an ideal nutrient source for all kinds of germs and parasites. Skincare products mostly serve for moisturizing and refatting the skin. Active ingredients are commonly added thereto, which are intended to regenerate the skin and for example to prevent and reduce the premature aging thereof (e.g. the appearance of fine lines and wrinkles).

The known active ingredients per se of cosmetic preparations include inorganic salts. Thus, for example, the cosmetic/therapeutic effectiveness of bathing in the Dead Sea has been known since time immemorial. However, inorganic salts, in particular sodium chloride, can be relatively difficult to incorporate into cosmetic preparations at higher concentrations. In emulsion systems, there is a risk of phase separation and even in aqueous systems there is a risk of salt crystals forming as a result of desiccation. This formation of salt crystals occurs in particular at the dispensing apertures of the packaging in which the preparation is stored, which can result in poorer re-closure of the packaging, whereby this phenomenon is further enhanced.

Cleansing or care wipes impregnated with salt-containing preparations are also known in the prior art. Such wipes are disclosed, for example, in DE 10234256, EP 0937453, WO 99/02128, DE 69601705 and DE 69506912. As these wipes are usually presented in relatively large quantities in storage containers which are not airtight, the phenomenon of "salt crust formation" is particularly pronounced, since the cleansing wipes have a particularly large surface area which dries out correspondingly quickly.

It was therefore the object of the present invention to develop a sodium chloride-containing cosmetic preparation, the tendency of which to form salt crystals is significantly reduced. In particular, the object was to develop cosmetic cleansing wipes, the impregnation of which comprises sodium chloride, in which salt crystal formation is suppressed.

SUMMARY OF THE INVENTION

Surprisingly, the object is achieved by a cosmetic preparation containing a) one or more alkane diols selected from the group of the compounds propylene glycol, butylene glycol, 2-methylpropane-1,3-diol, glyceryl caprylate, polyglyceryl-2 caprate, ethylhexylglycerin, 1,2-pentanediol, 1,2-hexanediol, 1,2-octanediol and/or 1,2-decanediol and b) sodium chloride at a concentration of 0.25 to 5% by weight, based on the total weight of the preparation.

In this case, a sodium chloride concentration of 0.5 to 2.5% by weight, based on the total weight of the preparation, is preferred in accordance with the invention.

With this sodium chloride concentration, the sodium chloride content is significantly above the salt content of the fully demineralized (DM) water normally used in cosmetic preparations. The content is also above the content of drinking water (for example, that of the drinking water of the Borstelbek groundwater works of Hamburg water, which has a content of 0.001% by weight sodium (average value for the year 2015). The limit for drinking water is 0.02% by weight).

Due to the active ingredient combination of sodium chloride and alkanediols according to the invention, the formation of salt crystals is suppressed to such an extent that it is also possible to incorporate significantly higher concentrations of sodium chloride in the preparations in a stable (in particular desiccation-stable) form. As a result, significantly more effective cosmetic preparations are obtained. For instance, when using the preparations, it could be observed, surprisingly, that for example the barrier lipid content in the stratum corneum (in particular the content of the ceramides 1, 3, 4, 5, 6 and 7) is significantly increased.

Not least, the preparations according to the invention have an unusually high microbial stability (both against bacteria and against fungi (e.g. yeasts)), which is significantly above the microbial stability of the alkane diols.

It is advantageous according to the invention if the total concentration of the alkane diols a) is from 0.05 to 20% by weight, based on the total weight of the preparation. The preferred use concentration according to the invention (total concentration of alkane diols a)) is from 0.1 to 10% by weight, based on the total weight of the preparation.

Embodiments of the present invention that are preferred in accordance with the invention are characterized in that the alkane diols used are one or more compounds selected from the group of the compounds 2-methylpropane-1,3-diol, ethylhexylglycerin, glyceryl caprylate, polyglyceryl-2 caprate, 1,2-pentanediol, 1,2-hexanediol, 1,2-octanediol and/or 1,2-decanediol.

Embodiments of the present invention that are particularly preferred in accordance with the invention are characterized in that the alkane diol used is ethylhexylglycerin.

It is advantageous in accordance with the invention if the preparation according to the invention comprises phenoxyethanol.

In such a case, it is advantageous in accordance with the invention if the preparation comprises phenoxyethanol at a concentration of 0.05 to 1% by weight, based on the total weight of the preparation. The use concentration preferred in accordance with the invention in this case is from 0.2 to 1% by weight, based on the total weight of the preparation.

Particularly preferred in accordance with the invention is therefore a preparation comprising a combination of ethylhexylglycerin and phenoxyethanol. In such a case, it is advantageous according to the invention to use ethylhexylglycerin at a concentration of 0.05 to 1% by weight and phenoxyethanol at a concentration of 0.2 to 1% by weight, based on the total weight of the preparation.

A further particularly advantageous combination according to the invention is a mixture of 1 to 10% by weight butylene glycol, 0.1 to 1% by weight phenoxyethanol, 0.05 to 1% by weight ethylhexylglycerin and 0.5 to 2% by weight 2-methylpropane-1,3-diol.

Embodiments of the present invention which are advantageous according to the invention are characterized in that the preparation is free of parabens, isothiazolinones and 3-iodopropargyl N-butylcarbamate (IPBC).

It is also advantageous in the context of the present invention if the preparation according to the invention comprises ethanol, benzyl alcohol and/or 4-hydroxyacetophenone.

If the preparation according to the invention comprises ethanol, this is advantageously used according to the invention at a concentration of 1 to 10% by weight, based on the total weight of the preparation.

If the preparation according to the invention comprises benzyl alcohol, this is advantageously used according to the invention at a concentration of 0.1 to 1% by weight, based on the total weight of the preparation.

If the preparation according to the invention comprises 4-hydroxyacetophenone, this is advantageously used according to the invention at a concentration of 0.1 to 0.8% by weight, based on the total weight of the preparation.

The preparation according to the invention can advantageously be in two forms: in the form of an aqueous preparation or an emulsion or hydrodispersion.

If the preparation is in the form of an aqueous preparation, the water content of the preparation according to the invention is advantageously from 60 to 98% by weight, based on the total weight of the preparation.

If the preparation according to the invention is in the form of an emulsion, it is preferred according to the invention if the preparation is in the form of an O/W emulsion.

In such a case, the embodiments of the invention that are advantageous in accordance with the invention are characterized in that the preparation comprises one or more emulsifiers selected from the group of the compounds polyglyceryl-10 stearate, glyceryl stearate citrate, glyceryl stearate, glyceryl stearate (self-emulsifying), polyglyceryl-3 methylglucose distearate, sodium cetearyl sulfate, potassium cetyl phosphate, sodium stearoyl glutamate, triceteareth-4 phosphate, stearic acid, stearate salts, cetearyl sulfosuccinates.

The total concentration of these emulsifiers in the preparation according to the invention in this case is advantageously from 0.5 to 5% by weight, based on the total weight of the preparation.

Particular preference in this case is given to using the emulsifier polyglyceryl-3 methylglucose distearate (INCI: Polyglyceryl-3 Methylglucose Distearate).

If the preparation according to the invention is in the form of an emulsion, the lipid phase of this emulsion may comprise the fats, oils and waxes which are usual in cosmetics.

Embodiments of the present invention which are advantageous according to the invention are also characterized in that the preparation comprises glycerol and/or panthenol.

If the preparation according to the invention comprises glycerol, it is advantageous according to the invention to use this substance at a concentration of 1 to 25% by weight, based on the total weight of the preparation.

If the preparation according to the invention comprises panthenol, it is advantageous according to the invention to use this substance at a concentration of 0.5 to 10% by weight, based on the total weight of the preparation.

It is particularly advantageous in the context of the present invention if the preparation according to the invention is free of polyethylene glycol, polyethylene glycol ethers and polyethylene glycol esters (so-called PEG derivatives).

It is advantageous according to the invention if the preparation according to the invention comprises vinylpyrrolidone/hexadecene copolymer (INCI: VP/Hexadecene Copolymer) and/or acrylate/C10-30 alkyl acrylate crosslinked polymer (INCI: Sodium Acrylates/C10-30 Alkyl Acrylate Crosspolymer).

If the preparation according to the invention comprises vinylpyrrolidone/hexadecene copolymer (INCI: VP/Hexadecene Copolymer), it is advantageous according to the invention to use this substance at a concentration of 0.05 to 0.5% by weight, based on the total weight of the preparation.

If the preparation according to the invention comprises acrylate/C10-30 alkyl acrylate crosslinked polymer (INCI: Sodium Acrylates/C10-30 Alkyl Acrylate Crosspolymer), it is advantageous according to the invention to use this substance at a concentration of 0.05 to 0.5% by weight, based on the total weight of the preparation.

It is also advantageous according to the invention if the preparation according to the invention comprises xanthan gum, sclerothium gum, cellulose derivatives and/or carragenan.

In accordance with the invention, preparations are also preferred which are free of 2-ethylhexyl 2-cyano-3,3-diphenylacrylate; 2-ethylhexyl 4-methoxycinnamate; isoamyl 4-methoxycinnamate, 2-hydroxy-4-methoxybenzophenone; 2-hydroxy-4-methoxy-4'-methylbenzophenone; 3-(4-methylbenzylidene)camphor, 3-benzylidene camphor, 2-phenylbenzimidazole-5-sulfonic acid and salts thereof; phenylene-1,4-bis(2-benzimidazyl)-3,3'-5,5'-tetrasulfonic acid salts; 1,4-di(2-oxo-10-sulfo-3-bornylidenemethyl)benzene salts; 4-(2-oxo-3-bornylidenemethyl)benzenesulfonic acid salts and 2-methyl-5-(2-oxo-3-bornylidenemethyl) sulfonic acid salts.

Advantageous embodiments according to the invention are also characterized in that the preparation comprises one or more perfumes selected from the group of the compounds limonene, citral, linalool, alpha-isomethyl ionone, geraniol, citronellol, 2-isobutyl-4-hydroxy-4-methyltetrahydropyran, 2-tert-pentylcyclohexyl acetate, 3-methyl-5-phenyl-1-pentanol, 7-acetyl-1,1,3,4,4,6-hexamethyltetralin, adipic acid diesters, alpha-amylcinnamaldehyde, alpha-methyl ionone, amyl C butylphenylmethylpropionalcinnamal, amyl salicylate, amylcinnamyl alcohol, anise alcohol, benzoin, benzyl alcohol, benzyl benzoate, benzyl cinnamate, benzyl salicylate, bergamot oil, bitter orange oil, butylphenyl methylpropional, cardamom oil, cedrol, cinnamal, cinnamyl alcohol, citronellyl methylcrotonate, lemon oil, coumarin, diethyl succinate, ethyl linalool, eugenol, Evernia furfuracea extract, Evernia prunastri extract, ethylene brassylate, farnesol, guaiac wood oil, hexylcinnamal, hexyl salicylate, hydroxycitronellal, lavender oil, limonene oil, linayl acetate, mandarin oil, menthyl PCA, methylheptenone, nutmeg oil, rosemary oil, sweet orange oil, terpineol, tonka bean oil, triethyl citrate, vanillin.

Furthermore, it is advantageous according to the invention if the preparation comprises organic acids, such as citric acid for example. This can also be wholly or partly present as citrate salt.

If the preparation according to the invention comprises citric acid, it is advantageous according to the invention to use this substance at a concentration of 0.1 to 1% by weight, based on the total weight of the preparation.

Advantageous embodiments in accordance with the invention are also characterized in that the preparation comprises one or more active ingredients selected from the group of the compounds gylcyrrhetic acid, urea, arctiin, alpha-lipoic acid, folic acid, phytoene, D-biotin, coenzyme Q10, hyaluronic acid, alpha-glucosylrutin, carnitine, carnosine, caffeine, natural and/or synthetic isoflavonoids, glyceryl glucoside, creatine, creatinine, taurine, β-alanine and/or licochalcone A, tocopherol, tocopherol acetate, vitamin C, vitamin C derivatives (especially the palmitate), *Glycyrrhiza inflata* root extract, magnolia extract, aloe vera, urea, *Arctium lappa* fruit extract.

In accordance with the invention, a cosmetic cleansing wipe is also impregnated with a preparation according to the invention, as described above.

It is advantageous in accordance with the invention in this case if the cleansing wipe is in the form of a nonwoven fabric comprising viscose fibers.

In principle, the nonwoven form is the preferred form of wipe according to the invention. In addition to wipe materials which consist of 100% viscose, mixed fiber structures of viscose and polyethylene terephthalate (PET) are also advantageous according to the invention. In such a case, the preferred blending ratio of viscose to PET is 30:70% by weight of the wipe material.

Another advantageous wipe material according to the invention (preferably nonwoven) is cellulose. Lyocell is used in this case as preferred cellulose in accordance with the invention.

Cellulose can also be used advantageously according to the invention as 100% wipe material or as a mixed fiber structure with polyethylene terephthalate (PET). In such a case, the preferred blending ratio of cellulose to PET is 25:75% by weight of the wipe material.

Advantageously in accordance with the invention, the degree of impregnation of the wipe, i.e. the ratio by weight of cosmetic preparation (=liquid impregnation) and wipe material is from 2 to 6, preferably from 2.2 to 3.7 and particularly preferably from 2.5 to 3.1.

DETAILED DESCRIPTION OF EMBODIMENTS OF THE INVENTION

Examples

The examples below are intended to illustrate the present invention without limiting it. Unless otherwise stated, all quantitative data, fractions and percentages are based on the weight and the total amount or on the total weight of the preparations.

Aqueous Preparations, Examples

|  | A | B | C |
|---|---|---|---|
| PEG 40 Hydrogenated Castor Oil | 1 |  | 0.5 |
| Decyl Glucoside |  | 0.2 |  |
| Sodium Cocoyl Glutamate |  |  | 0.02 |
| Ethylhexylglycerin | 0.5 | 0.1 |  |
| Caprylyl Glycol |  |  | 0.35 |
| Hexanediol |  |  | 0.2 |
| Methylpropanediol |  | 3 |  |
| Phenoxyethanol |  |  | 0.6 |
| Propylene glycol |  | 2 |  |
| Glycerol | 25 | 10 | 5 |
| Glyceryl glucoside | 10 |  |  |
| Sorbitol |  | 0.5 |  |
| Citric acid |  |  | 0.07 |
| Panthenol |  | 5 |  |
| Perfume | 0.3 |  | 0.1 |
| Sodium chloride | 2.5 | 1 | 1.5 |
| Almond oil | 0.1 |  |  |
| Water | to 100 | to 100 | to 100 |
| Alcohol | 10 |  |  |
| Poloxamer 124 |  | 0.2 |  |

Hydrodispersions Examples

| INCI | A | B | C | D | E |
|---|---|---|---|---|---|
| Maris Sal/Sodium Chloride | 2.5 | 2.5 | 1.5 | 1 | 2.5 |
| Ethylhexylglycerin |  | 0.25 | 0.5 | 0.2 | 0.115 |
| Caprylic/Capric Triglyceride |  | 3 |  | 2.5 |  |
| Helianthus Annuus Seed Oil |  |  | 3 |  |  |
| Isopropyl Palmitate | 3 |  |  |  | 3.5 |
| Sodium cetearyl sulfate | 0.2 | 0.4 |  |  |  |
| Glyceryl Stearate SE | 0.15 | 0.15 |  |  |  |
| Glyceryl Stearate Citrate |  |  | 0.5 | 0.75 | 0.5 |
| Glyceryl Caprylate | 0.25 | 0.3 | 0.15 | 0.3 | 0.3 |
| VP/Hexadecene Copolymer |  | 0.25 |  | 0.25 |  |
| Perfume | 0.25 | 0.3 | 0.1 |  | 0.25 |
| Butylene Glycol |  | 2 | 1 | 4 | 1 |
| Glycerol | 3 |  |  | 1 |  |
| Citric Acid | 0.18 | 0.19 | 0.185 | 0.18 | 0.17 |
| Sodium Benzoate | 0.35 | 0.2 |  | 0.4 | 0.25 |
| Benzyl Alcohol | 0.15 |  | 0.8 |  | 1 |
| Hydroxyethylcellulose | 0.1 | 0.2 | 0.15 | 0.3 | 0.05 |
| Xanthan Gum | 0.3 | 0.2 | 0.2 | 1 | 0.2 |
| Aqua | to 100 | to 100 | to 100 | to 100 | to 100 |

Hydrogels

|  | A | B |
|---|---|---|
| PEG-40 Hydrogenated Castor Oil | 1 | 0.4 |
| Perfume | 0.3 |  |
| Polyglyceryl-2 Caprate |  |  |
| Ethylhexylglycerin | 0.2 | 0.5 |
| Caprylyl Glycol | 0.2 |  |
| Decanediol |  | 0.3 |
| Hexanediol |  |  |
| Methylpropanediol | 2.5 | 3 |
| Phenoxyethanol | 0.6 |  |
| Butylene glycol | 10 | 2 |
| Glycerol | 5 | 10 |
| Glyceryl glucoside | 10 |  |
| Panthenol |  | 5 |
| Xanthan Gum | 0.3 | 0.15 |
| Hydroxypropyl Methylcellulose |  | 0.15 |
| Jojoba oil | 0.1 | 0.15 |
| *Aloe Vera* |  | 0.05 |
| Sodium chloride | 2.5 | 3.5 |
| Water | to 100 | to 100 |

Emulsions Examples

|  | A | B | C |  |
|---|---|---|---|---|
| Sodium cetearyl sulfate | 1 | 0.15 |  |  |
| Glyceryl stearate citrate |  |  | 2.5 |  |
| Peg-40 stearate |  |  |  | 1.5 |
| Glyceryl stearate | 1.5 | 3.0 | 1 | 3 |
| Glyceryl stearate SE |  | 1.7 |  |  |
| Stearic acid | 2.2 |  |  |  |
| Octyldodecanol | 2 | 6 | 4 | 5 |
| Shea butter | 2 | 3 | 5 | 1 |
| Hydrogenated Coco Glycerides | 3 | 1 |  | 2 |
| Caprylic Capric Triglyceride | 5 | 4 |  | 4 |
| Cetyl alcohol | 2 | 4 | 1.5 | 2 |
| Polyglyceryl-2 Caprate |  | 0.3 | 0.3 |  |
| Ethylhexylglycerin | 0.3 | 0.2 |  |  |
| Caprylyl Glycol | 0.25 |  | 0.35 |  |
| Pentanediol |  | 0.3 |  |  |
| Hydroxyacetophenone | 0.3 |  | 0.2 |  |
| Glyceryl Caprylate |  | 3 |  |  |
| Phenoxyethanol | 0.6 |  | 0.3 | 0.6 |
| Butylene glycol | 2 | 2 |  | 3 |
| Glycerol | 5 | 10 | 5 | 7 |
| Glyceryl glucoside | 5 |  | 5 |  |
| Panthenol | 5 | 2 | 1 |  |
| Xanthan Gum | 0.1 | 0.15 | 0.1 |  |
| Carrageenan |  | 0.15 |  |  |
| Sodium Carbomer |  |  | 0.3 | 0.3 |
| Microcrystalline Cellulose + Cellulose Gum | 0.1 |  | 0.1 |  |
| Sodium chloride | 2.5 | 3.5 | 0.5 | 1 |
| Water | to 100 | to 100 | to 100 | to 100 |
| Perfume |  |  |  |  |

What is claimed is:

1. A cosmetic preparation, wherein the preparation is suitable for cleansing of skin and/or caring for skin and comprises
   (a) one or more alkanediols selected from propylene glycol, butylene glycol, 2-methylpropane-1,3-diol, glyceryl caprylate, polyglyceryl-2 caprate, ethylhexylglycerin, 1,2-pentanediol, 1,2-hexanediol, 1,2-octanediol, 1,2-decanediol and
   (b) from 1.5% to 5% by weight of sodium chloride, based on a total weight of the preparation;
   and wherein the preparation is free of parabens, isothiazolinones and 3-iodopropargyl N-butylcarbamate (IPBC), is free of 2-ethylhexyl 2-cyano-3,3-diphenylacrylate; 2-ethylhexyl 4-methoxycinnamate; isoamyl 4-methoxycinnamate, 2-hydroxy-4-methoxybenzophenone; 2-hydroxy-4-methoxy-4'-methylbenzophenone; 3-(4-methyl-benzylidene)camphor, 3-benzylidene camphor, 2-phenylbenzimidazole-5-sulfonic acid and salts thereof; phenylene-1,4-bis(2-benzimidazyl)-3,3'-5,5'-tetrasulfonic acid salts; 1,4-di(2-oxo-10-sulfo-3-bornylidenemethyl)benzene salts; 4-(2-oxo-3-bornylidenemethyl)benzenesulfonic acid salts and 2-methyl-5-(2-oxo-3-bornylidenemethyl) sulfonic acid salts, and also is free of polyethylene glycol, polyethylene glycol ethers and polyethylene glycol esters.

2. The preparation of claim 1, wherein the preparation further comprises phenoxyethanol.

3. The preparation of claim 1, wherein (a) is present in a concentration of from 0.05% to 20% by weight, based on a total weight of the preparation.

4. The preparation of claim 1, wherein the preparation further comprises one or both of ethanol and 4-hydroxyacetophenone.

5. The preparation of claim 1, wherein the preparation is present in the form of a hydrodispersion.

6. The preparation of claim 1, wherein the preparation further comprises panthenol.

7. The preparation of claim 1, wherein the preparation further comprises acrylate/C10-30 alkyl acrylate crosslinked polymer.

8. A cosmetic preparation, wherein the preparation is suitable for cleansing of skin and/or caring for skin and comprises
   (a) one or more alkanediols selected from propylene glycol, butylene glycol, 2-methylpropane-1,3-diol, glyceryl caprylate, polyglyceryl-2 caprate, ethylhexylglycerin, 1,2-pentanediol, 1,2-hexanediol, 1,2-octanediol, 1,2-decanediol, ethylhexylglycerin being present in a concentration of from 0.05 to 0.5% by weight, based on a total weight of the preparation, and
   (b) from 0.25% to 5% by weight of sodium chloride, based on the total weight of the preparation;
   and wherein the preparation is free of parabens, isothiazolinones and 3-iodopropargyl N-butylcarbamate (IPBC), is free of 2-ethylhexyl 2-cyano-3,3-diphenylacrylate; 2-ethylhexyl 4-methoxycinnamate; isoamyl 4-methoxycinnamate, 2-hydroxy-4-methoxybenzophenone; 2-hydroxy-4-methoxy-4'-methylbenzophenone; 3-(4-methyl-benzylidene)c amphor, 3-benzylidene camphor, 2-phenylbenzimidazole-5-sulfonic acid and salts thereof; phenylene-1,4-bis(2-benzimidazyl)-3,3'-5,5'-tetrasulfonic acid salts; 1,4-di(2-oxo-10-sulfo-3-bornylidenemethyl)benzene salts; 4-(2-oxo-3-bornylidenemethyl)benzenesulfonic acid salts and 2-methyl-5-(2-oxo-3-bornylidenemethyl) sulfonic acid salts, and also is free of polyethylene glycol, polyethylene glycol ethers and polyethylene glycol esters.

9. The preparation of claim 8, wherein from 1.5% % to 5% by weight of sodium chloride are present.

10. The preparation of claim 8, wherein the preparation further comprises phenoxyethanol.

11. The preparation of claim 8, wherein (a) is present in a concentration of from 0.05% to 20% by weight, based on a total weight of the preparation.

12. The preparation of claim 8, wherein the preparation further comprises one or both of ethanol and 4-hydroxyacetophenone.

13. The preparation of claim 8, wherein the preparation is present in the form of a hydrodispersion.

14. The preparation of claim 8, wherein the preparation further comprises panthenol.

15. The preparation of claim 8, wherein the preparation further comprises acrylate/C10-30 alkyl acrylate crosslinked polymer.

16. A cosmetic preparation, wherein the preparation is suitable for cleansing of skin and/or caring for skin and comprises, based on a total weight of the preparation, from 1% to 10% by weight of butylene glycol, from 0.1% to 1% by weight of phenoxyethanol, from 0.05% to 1% by weight of ethylhexylglycerin, from 0.5% to 2% by weight of 2-methylpropane-1,3-diol, and from 0.25% to 5% by weight of sodium chloride;
   and wherein the preparation is free of parabens, isothiazolinones and 3-iodopropargyl N-butylcarbamate (IPBC), is free of 2-ethylhexyl 2-cyano-3,3-diphenylacrylate; 2-ethylhexyl 4-methoxycinnamate; isoamyl 4-methoxycinnamate, 2-hydroxy-4-methoxybenzophenone; 2-hydroxy-4-methoxy-4'-methylbenzophenone; 3-(4-methyl-benzylidene)camphor, 3-benzylidene camphor, 2-phenylbenzimidazole-5-sulfonic acid and salts thereof; phenylene-1,4-bis(2-benzimidazyl)-3,3'-5,5'-tetrasulfonic acid salts; 1,4-di(2-oxo-10-sulfo-3-bornylidenemethyl)benzene salts; 4-(2-oxo-3-bornylidenemethyl)benzenesulfonic acid salts and 2-methyl-5-(2-oxo-3-bornylidenemethyl) sulfonic acid salts, and also is free of polyethylene glycol, polyethylene glycol ethers and polyethylene glycol esters.

17. The preparation of claim 1, wherein the preparation does not contain a silicon-containing compound.

18. The preparation of claim 8, wherein the preparation does not contain a silicon-containing compound.

19. The preparation of claim 1, wherein the preparation is not present in the form of a shampoo.

20. The preparation of claim 1, wherein the preparation, when applied to skin, increases a barrier lipid content of a stratum corneum.

\* \* \* \* \*